(12) United States Patent
Liu et al.

(10) Patent No.: US 12,163,121 B2
(45) Date of Patent: Dec. 10, 2024

(54) **MUTANTS OF *CORYNEBACTERIUM GLUTAMICUM* WITH EFFICIENT EXPRESSION OF EXOGENOUS PROTEINS AND METHOD OF USE THEREOF**

(71) Applicant: Jiangnan University, Wuxi (CN)

(72) Inventors: Xiuxia Liu, Wuxi (CN); Lihong Meng, Wuxi (CN); Yankun Yang, Wuxi (CN); Chunli Liu, Wuxi (CN); Ye Li, Wuxi (CN); Zhonghu Bai, Wuxi (CN)

(73) Assignee: Jiangnan University, Wuxi (CN)

( * ) Notice: Subject to any disclaimer, the term of this patent is extended or adjusted under 35 U.S.C. 154(b) by 270 days.

(21) Appl. No.: 17/389,360

(22) Filed: Jul. 30, 2021

(65) Prior Publication Data

US 2022/0056400 A1 Feb. 24, 2022

(30) Foreign Application Priority Data

Aug. 24, 2020 (CN) .......................... 202010859729.X

(51) Int. Cl.
| | | |
|---|---|---|
| *C12N 1/20* | (2006.01) | |
| *C07K 14/78* | (2006.01) | |
| *C07K 16/00* | (2006.01) | |
| *C12N 15/01* | (2006.01) | |
| *C12R 1/15* | (2006.01) | |

(52) U.S. Cl.
CPC .............. *C12N 1/205* (2021.05); *C07K 14/78* (2013.01); *C07K 16/00* (2013.01); *C12N 15/01* (2013.01); *C07K 2317/14* (2013.01); *C07K 2317/569* (2013.01); *C12R 2001/15* (2021.05)

(58) Field of Classification Search
CPC ........ C12N 1/205; C12N 15/01; C07K 14/78; C07K 16/00; C07K 2317/14; C07K 2317/569; C12R 2001/15
See application file for complete search history.

(56) References Cited

FOREIGN PATENT DOCUMENTS

| | | | | | |
|---|---|---|---|---|---|
| CN | 103946371 | A | * | 7/2014 | ............. C07K 14/34 |
| CN | 109576261 | A | * | 4/2019 | |
| CN | 109694841 | A | * | 4/2019 | |
| CN | 109937258 | A | * | 6/2019 | ............... C07K 1/12 |
| CN | 111909879 | A | * | 11/2020 | ............. C07K 14/78 |

OTHER PUBLICATIONS

Machine English translation of CN-103946371-A retrieved from eSpacenet (2022). (Year: 2022).*
Machine English translation of CN-109694841-A retrieved from eSpacenet (2022). (Year: 2022).*
Machine English translation of CN-109937258-A retrieved from eSpacenet (2022). (Year: 2022).*
Machine English translation of CN-111909879-A retrieved from eSpacenet (2022). (Year: 2022).*
Yim SS, Choi JW, Lee RJ, Lee YJ, Lee SH, Kim SY, Jeong KJ. Development of a new platform for secretory production of recombinant proteins in Corynebacterium glutamicum. Biotechnol Bioeng. Jan. 2016;113(1):163-72. doi: 10.1002/bit.25692. Epub Sep. 8, 2015. PMID: 26134574. (Year: 2015).*
Zhang W, Zhao Z, Yang Y, Liu X, Bai Z. Construction of an expression vector that uses the aph promoter for protein expression in Corynebacterium glutamicum. Plasmid. Nov. 2017;94:1-6. doi: 10.1016/j.plasmid.2017.09.001. Epub Oct. 3, 2017. PMID: 28986243. (Year: 2017).*
Sun M, Gao X, Zhao Z, Li A, Wang Y, Yang Y, Liu X, Bai Z. Enhanced production of recombinant proteins in Corynebacterium glutamicum by constructing a bicistronic gene expression system. Microb Cell Fact. May 26, 2020;19(1):113. doi: 10.1186/s12934-020-01370-9. PMID: 32456643; PMCID: PMC7251831. (Year: 2020).*
Machine translation of CN109576261A to English, [retrieved on Nov. 9, 2023]. Retrieved from Espacenet at <https://worldwide.espacenet.com/patent/search/family/065917907/publication/CN109576261A?q=cn109576261> (Year: 2023).*
Ma Y, Yang H, Chen X, Sun B, Du G, Zhou Z, Song J, Fan Y, Shen W. Significantly improving the yield of recombinant proteins in Bacillus subtilis by a novel powerful mutagenesis tool (ARTP): Alkaline a-amylase as a case study. Protein Expr Purif. Oct. 2015;114:82-8. doi: 10.1016/j.pep.2015.06.016. (Year: 2015).*

* cited by examiner

*Primary Examiner* — Louise W Humphrey
*Assistant Examiner* — John Paul Selwanes
(74) *Attorney, Agent, or Firm* — IDEA Intellectual Limited; Margaret A. Burke; Sam T. Yip

(57) ABSTRACT

The present invention provides a mutant strain of *Corynebacterium glutamicum* with efficient expression of exogenous proteins, which can solve the technical problem of low protein expression quantity of using *Corynebacterium glutamicum* as an exogenous protein expression host. The mutant strain of *Corynebacterium glutamicum* is deposited in the China General Microbiological Culture Collection Center (CGMCC), and the deposit number is CGMCC No. 20138. The mutant strain of *Corynebacterium glutamicum* in the present invention, verified by the expression of exogenous proteins, shows a significantly enhanced expression of both intracellular and secreted proteins when compared with its initial strain.

1 Claim, 4 Drawing Sheets
Specification includes a Sequence Listing.

MUTANTS OF *CORYNEBACTERIUM GLUTAMICUM* WITH EFFICIENT EXPRESSION OF EXOGENOUS PROTEINS AND METHOD OF USE THEREOF

CROSS-REFERENCES TO RELATED APPLICATIONS

This application claims priority from Chinese patent application number 202010859729.X filed on Aug. 24, 2020; the disclosure of which are incorporated herein by reference in their entirety.

FIELD OF THE INVENTION

The present invention relates to a mutant strain of *Corynebacterium glutamicum* with efficient expression of exogenous proteins and its application, which belongs to the field of bioengineering technology.

BACKGROUND OF THE INVENTION

*Corynebacterium glutamicum* is a gram-positive bacterium belonging to the Actinomycetales and the *Corynebacterium*. It is an important protein expression host. It has many advantages, such as endotoxin-free, high-density production and complete protein secretion system. At present, it has been used as a synthetic biological host cell to produce high value-added compounds and recombinant pharmaceutical proteins, such as glutamic acid and lysine. It is also used in food industry and animal feed production.

When *Corynebacterium glutamicum* serves as an exogenous protein expression host, the amount of protein expression is low. Therefore, it is necessary to perform mutagenesis screening for *Corynebacterium glutamicum* to make it more efficient in expressing exogenous protein.

SUMMARY OF THE INVENTION

The present invention provides a mutant strain of *Corynebacterium glutamicum* with efficient expression of exogenous proteins, which can solve the technical problem of low protein expression quantity when *Corynebacterium glutamicum* is used as an exogenous protein expression host.

The technical scheme is a mutant strain of *Corynebacterium glutamicum* with efficient expression of exogenous proteins, which is deposited in the China General Microbiological Culture Collection Center (CGMCC), and the deposit number is CGMCC No. 20138.

Further, the mutant strain of *Corynebacterium glutamicum* is obtained by atmospheric and room temperature plasma (ARTP) mutagenesis and screening using *Corynebacterium glutamicum* with the deposited number of CGMCC1.15647 as an initial strain.

The present invention also provides a method of use of the above-mentioned mutant strain of *Corynebacterium glutamicum* for the expression of exogenous proteins.

Further, the exogenous protein is a single domain of heavy chain antibody or N-terminal pro-peptide of human procollagen type I.

Variable domain of heavy chain of heavy-chain antibody (VHH) is a single domain antibody composed of a heavy chain variable region. The heavy chain variable region is derived from a heavy chain antibody that naturally lacks the light chain in camel serum.

The mutant strain of *Corynebacterium glutamicum* in the present invention, verified by the expression of exogenous proteins, shows a significantly enhanced expression of both intracellular and secreted proteins when compared with the initial strain.

Biological Deposit Instructions
Latin scientific name: *Corynebacterium glutamicum*
Deposited center: China General Microbiological Culture Collection Center
The abbreviation of the deposited center: CGMCC
The address of the deposited center: Institute of Microbiology, Chinese Academy of
Sciences, No. 3, No. 1 Institute, Beichen West Road, Chaoyang District, Beijing.
The deposit date: Jun. 24, 2020
The deposit number: CGMCC NO. 20138

BRIEF DESCRIPTION OF THE DRAWINGS

FIG. 2a is the initial strain containing pXMJ19-EGFP; FIG. 2b is the mutant strain containing pXMJ19-EGFP; the rectangular boxed section in the upper right corner shown in the FIGS. 2a and 2b representing the collected strain.

In FIG. 4a, lane 1: the disrupted supernatant of *Corynebacterium glutamicum* initial strain, lane 2: the disrupted supernatant of initial strain containing pXMJ19-VHH, lane 3: the disrupted supernatant of mutant strain BZH-MLH-YB5 containing pXMJ19-VHH. In FIG. 4b, lane 1: secretory supernatant of the initial strain of *Corynebacterium glutamicum* initial strain, lane 2: the secretory supernatant of initial strain containing pXMJ19-PINP, lane 3: the secretory supernatant of mutant strain BZH-MLH-YB5 containing pXMJ19-PINP.

DETAILED DESCRIPTION

Figure 1:
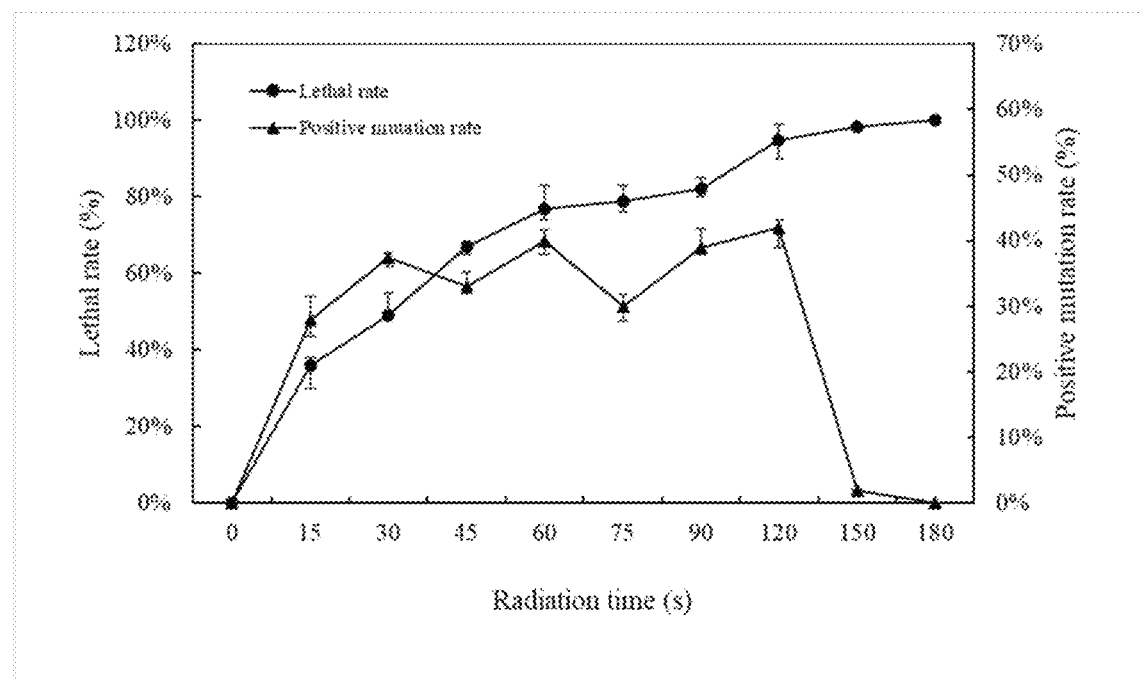
FIG. 1 shows a relationship between positive mutation rate, lethal rate and mutagenetic treatment time.

The *E. coli* DH5α used in the following examples or application examples was purchased from TAKARA.

The *Corynebacterium glutamicum* CGMCC 1.15647 used in the following examples or application examples was publicly deposited in 2016, and a person skilled in the art is able to acquire the existing bacterial strain prior to the application date.

The vector backbone pXMJ19 used in the following examples or application examples was purchased from Biovector; catalog number is BiovectorpXMJ19.

The restriction endonucleases EcoR V, XhoI, HindIII and BamHI used in the following examples or application examples were purchased from TaKaRa Company, and the catalog numbers are 1612, 1635, 1615, and 1605, respectively.

The plasmid extraction kits, gel purify and column purify kits used in the following examples or application examples were purchased from Axygen, and the catalog numbers are AP-MD-P-10, AP-GX-250, AP-PCR-250, respectively.

The ligase, solutionI, used in the following examples or application examples was purchased from TaKaRa Company, catalog number is D6020A.

In the following examples or application examples, LB medium is used for culturing *E. coli*. The medium formula is: tryptone 10 g, yeast extract 5 g, NaCl 10 g, and deionized water 1 L.

In the following examples or application examples, LBB medium is used for culturing *Corynebacterium glutamicum*. The medium formula is: tryptone 10 g, yeast extract 5 g, NaCl 10 g, brain-heart infusion 10 g, and deionized water 1 L.

In the following examples or application examples, LBHIS medium is used for culturing *Corynebacterium glutamicum*. The medium formula is: tryptone 5 g, yeast extract 2.5 g, NaCl 5 g, brain-heart infusion 18.5 g, sorbitol 91 g, deionized water 1 L.

1. Mutant Strains Basic Information

A mutant strain of *Corynebacterium glutamicum* with efficient expression of exogenous proteins, named BZH-MLH-YB5, is provided. The mutant strain of *Corynebacterium glutamicum* is deposited in the in the China General Microbiological Culture Collection Center, and the deposit number is CGMCC No. 20138.

2. Preparation of Mutant Strains

The pXMJ19-EGFP plasmid was introduced into *Corynebacterium glutamicum* CGMCC1.15647 as an initial strain. After resuscitation, the transformed bacteria were spread on solid LBB plates containing 15 μg/mL chloramphenicol, then incubated at 30° C. for 18 hours and selected a single colony in 30 mL of LBB liquid medium. Incubated at 30° C. for 10 hours, and transferred to 10 mL of LBB liquid medium, when the initial $OD_{600}$ was 0.2, then cultured for about 2 h to increase the $OD_{600}$ to 0.6, then take 10 uL bacterial liquid on the slide. ARTP mutagenesis was performed under the conditions of power of 100W, air flow of 10SLM, and time of 120s to induce random mutations to the CGMCC1.15647 initial strain. After mutagenesis, it was placed in a 1.5 ml centrifuge tube with 1 ml PBS and eluted by oscillation. Using the BD FACS AriaIII flow cytometer to perform flow cytometric sorting on the bacterial solution and the fluorescence intensity as the sorting signal to screen about $10^2$-$10^1$ strains with higher fluorescence intensity. Coating the obtained bacterial solution on the LBB solid plate containing 15 μg/mL chloramphenicol and after culturing at 30° C. for 12 h, single colony was selected in 48 well plate for screening out 50 strains. The strain was transferred to a 100 mL shake flask containing 10 mL of LBB liquid for re-screening. The strain with the highest fluorescence intensity was selected, and the obtained strain was used as the initial strain for the next mutagenesis. After repeated mutagenesis and sorting, the mutant strain with the highest fluorescence intensity was obtained and preserved.

2.1 Preparation of pXMJ19-EGFP Plasmid

Using pXMJ19 plasmid as the backbone, the plasmid was digested with EcoRV and XhoI for removing the lacI part, and the backbone part was purified by gel. Performing PCR with the forward and reverse primers F and R to generate a tac promoter fragment, purified by column. The tac promoter fragment was digested by the same enzymes and ligated with the backbone to form the recombinant pXMJ19 plasmid. The recombinant pXMJ19 plasmid was digested with HindIII and BamHI, and the digested plasmid fragments were purified by gel. The green fluorescent protein fragment was obtained by PCR using primers EGFP-F and EGFP-R. The gene sequence of EGFP, such as SEQ ID NO: 1, was digested with the same enzyme and ligated with the digested pXMJ19 by a ligase to obtain the recombinant pXMJ19-EGFP plasmid.

F: GATATCAACGTAAATGCCGCTTCGCC (SEQ ID NO: 4);
R: CTCGAGAATTAATTCTGTTTCCTGTGT (SEQ ID NO: 5);
EGFP-F: AAGCTTATGGTGAGCAAGGGC (SEQ ID NO: 6);
EGFP-R: GGATCCTTACTTGTACAGCTCGT (SEQ ID NO: 7).

2.2 Determine the Best Mutation Time

Different time points, t=0, 15, 30, 45, 60, 75, 90, 120, 150s, 180s, were selected to determine the positive mutation rate and lethal rate. The results are shown in FIG. 1. When the mutagenesis time was 120s, the positive mutation rate reached a maximum of about 42%, and the lethal rate was about 95%. Therefore, 120s was selected as the best mutagenesis time.

2.3 Screening of Mutant Strains by Flow Cytometry

Figure 2A:
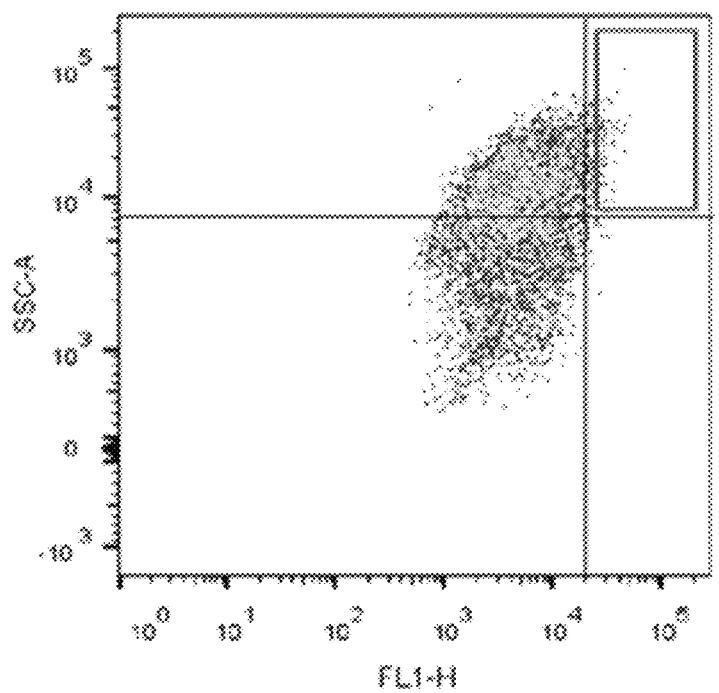
FIGS. 2a and 2b show results of flow sorting mutant strains.
Figure 2B:
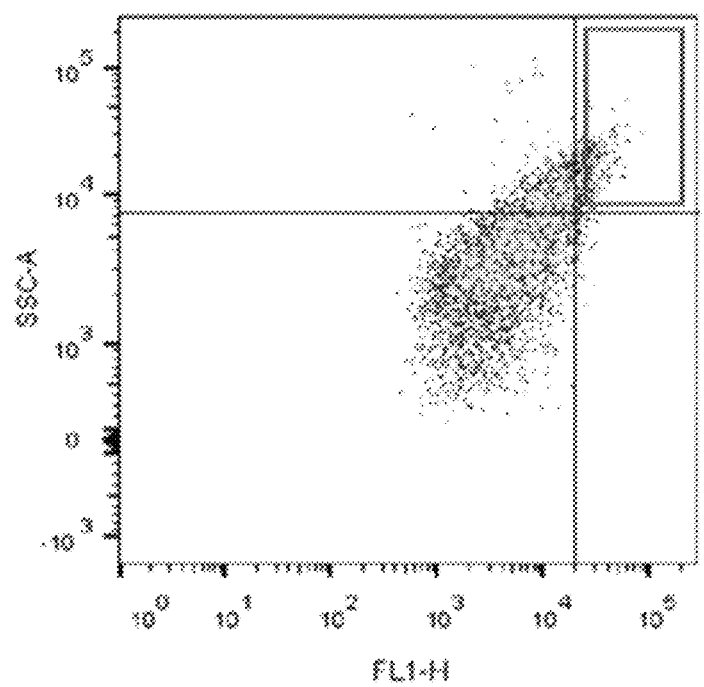

As shown in FIGS. 2a-2b, the fluorescence intensity of the mutant strain is significantly shifted to the right and the proportion of the collected highly fluorescent strains is obviously increased, compared with the initial strain.

2.4 Screening the Best Mutant Strain

After three rounds of mutagenesis and sorting, the mutant strain BZH-MLH-YB5 was screened. The fluorescence intensity of the mutant was nearly one-fold higher than the initial strain. However, the fluorescence intensity of the mutant strain obtained after four, five or more rounds of mutagenesis and sorting was lower than that of the mutant strain BZH-MLH-YB5, suggesting that the mutant strain BZH-MLH-YB5 is the best mutagenic strain.

Figure 3:
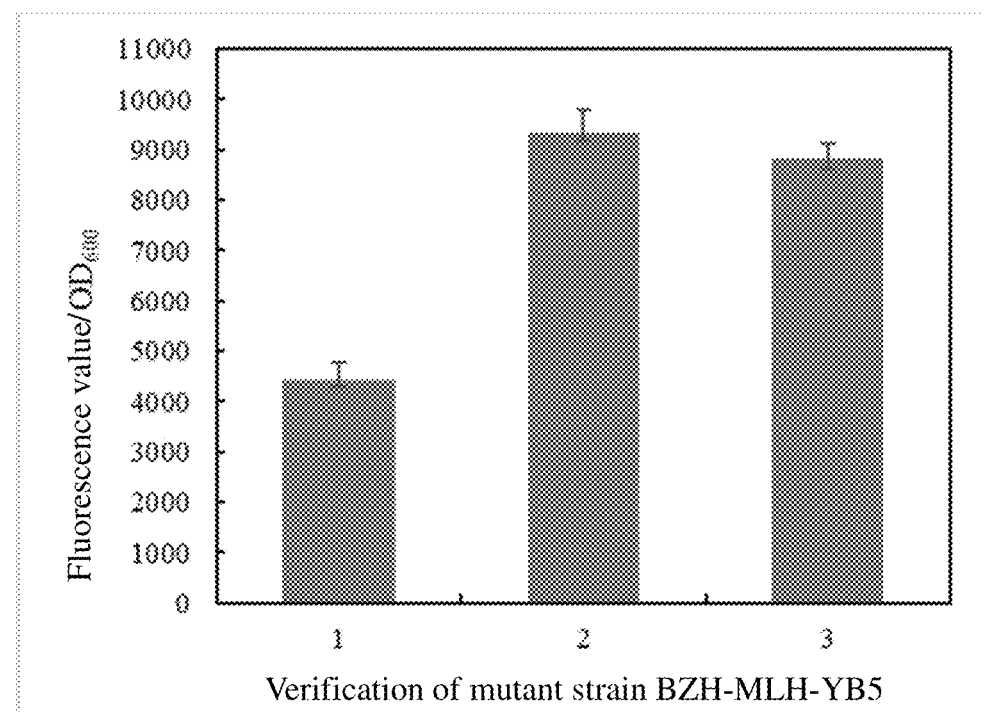
FIG. 3 shows the result of the verification of the mutagenic strain BZH-MLH-YB5, the number 1 is the initial strain containing pXMJ19-EGFP, the number 2 is the mutant strain BZH-MLH-YB5 containing pXMJ19-EGFP, and the number 3 is the mutant strain BZH-MLH-YB5 reintroduced with pXMJ19-EGFP after 4 times of subcultures.

2.5 Stability Test of Mutant Strain a. The stability of the mutant strain BZH-MLH-YB5 was verified, sub-cultured 10 times, and the fluorescence value of each generation was measured. The fluctuation range of the fluorescence value of each generation was within 10%, which was basically stable.

b. Plasmid loss was measured by sub-culturing the mutant strain BZH-MLH-YB5 four times in a growth medium without resistance then re-introducing it with pXMJ19-EGFP for detecting the fluorescence intensity. As shown in FIG. 3, the fluorescence value is still one-fold higher, which is basically consistent with the fluorescence intensity of the mutant strain BZH-MLH-YB5. Therefore, it is confirmed that the mutant strain BZH-MLH-YB5 is the cause of the significant increase in protein expression, not the change in pXMJ19-EGFP.

2.6 Exogenous Protein Expression Experiment of Mutant Strains 2.6.1 Intracellular Protein VHH Expression Experiment Preparation of recombinant pXMJ19-VHH plasmid: digesting the recombinant plasmid pXMJ19, the backbone, with HindIII and EcoRI, and purifying it by gel to obtain the digested plasmid fragment. Performing PCR with VHH-F and VHH-R to obtain the VHH fragments, and the gene sequence of VHH is listed in SEQ ID NO: 2. The VHH fragments are digested with the same enzyme and ligated with the digested plasmid fragment by a ligase to obtain the recombinant pXMJ19-VHH plasmid.

VHH-F: AAGCTTATGCAGGTCCAACTGCAAGAAAG (SEQ ID NO: 8);
VHH-R: GAATTCTCAGTGGTGGTGGTGGTGGTGTGAAGAGACGGTCACC (SEQ ID NO: 9).

Figure 4A:
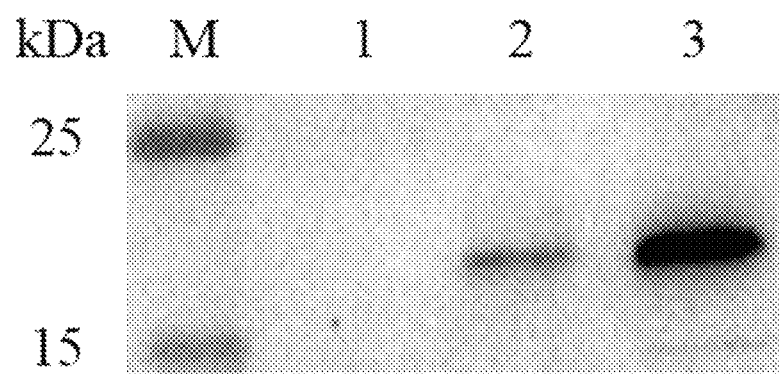
FIGS. 4a and 4b show the Western Blot electrophoresis of the proteins expressed by the recombinant strains.

The pXMJ19-VHH plasmid was transformed into the mutant strain BZH-MLH-YB5 and the initial strain CGMCC1.15647, and the obtained transformants were individually cultured for 48 hours. The cells were disrupted by sonication, and the supernatant was centrifuged and analyzed by Western blot, and the obtained band pattern is shown in FIG. 4a. Image J is used to perform gray-scale analysis of the band pattern, and the analysis results are shown in Table 1a.

TABLE 1a

| Lane | Area | Average | Minimum | Max | Optical density value |
|---|---|---|---|---|---|
| 2 | 646 | 79.167 | 24 | 120 | 51142 |
| 3 | 1384 | 174.408 | 43 | 210 | 241381 |

In FIG. 4a, comparing the mutant strain with the initial strain, the expression of intracellular protein was significantly enhanced. From Table 1a, the mutant strain showed a 3.7-fold increase in VHH protein expression compared with the initial strain.

2.6.2 Secreted Protein PINP Expression Experiment

The original plasmid pXMJ19 was used as the backbone to construct inducible plasmid pXMJ19-PINP. The original plasmid pXMJ19 is digested with HindIII and EcoRI and purified by gel to obtain the digested plasmid fragment. PINP-F and PINP-R were used for performing PCR to obtain PINP fragments. The gene sequence of PINP is listed in SEQ ID NO: 3. PINP fragments were digested with the same enzyme and ligated with the digested plasmid fragment by a ligase to obtain the inducible pXMJ19-PINP plasmid.

PINP-F: AAGCTTATGCAAGAAGAAGGC-CAAGTGGA (SEQ ID NO: 10);
PINP-R: GAATTCTTACTGGCCGCCGTGGT-GATGGTG (SEQ ID NO: 11).

Figure 4B:
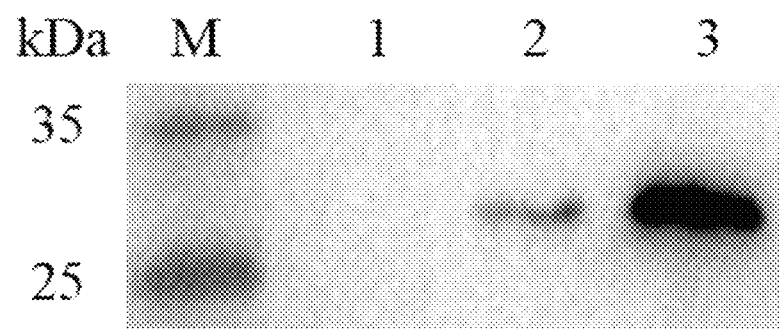

The pXMJ19-VHH plasmid was transformed into the mutant strain BZH-MLH-YB5 and the initial strain CGMCC1.15647, and the obtained transformants were individually cultured for 48 hours. The supernatant was centrifuged and analyzed by Western blot, and the obtained band pattern is shown in FIG. 4b. Image J is used to perform gray-scale analysis of the band pattern, and the analysis results are shown in Table 1b.

TABLE 1b

| Lane | Area | Average | Minimum | Max | Optical density value |
|---|---|---|---|---|---|
| 2 | 720 | 65.628 | 13 | 157 | 47252 |
| 3 | 1064 | 200.36 | 69 | 225 | 213183 |

In FIG. 4b, comparing the mutant strain with the initial strain, the expression of secreted protein was significantly enhanced. From Table 1b, the mutant strain showed a 3.5-fold increase in PINP protein expression compared with the initial strain.

SEQUENCE LISTING

This application contains a sequence listing which has been submitted in ASCII text file via EFS-Web and is hereby incorporated by reference in its entirety. The ASCII-formatted sequence listing, is named P2059US00_sequence listing.txt, and is 4,402 bytes in size.

SEQ ID NO: 1 in the sequence listing file is the corresponding gene sequence of EGFP, SEQ ID NO: 2 in the sequence listing file is the corresponding gene sequence of VHH, and SEQ ID NO: 3 in the sequence listing file is the corresponding gene sequence of PINP.

SEQ ID NO: 4 in the sequence listing file is the corresponding forward primer F, SEQ ID NO: 5 in the sequence listing file is the corresponding reverse primer R.

SEQ ID NO: 6 in the sequence listing file is the corresponding primer EGFP-F, SEQ ID NO: 7 in the sequence listing file is the corresponding primer EGFP-R.

SEQ ID NO: 8 in the sequence listing file is the corresponding primer VHH-F, SEQ ID NO: 9 in the sequence listing file is the corresponding primer VHH-R.

SEQ ID NO: 10 in the sequence listing file is the corresponding primer PINP-F, SEQ ID NO: 11 in the sequence listing file is the corresponding primer PINP-R.

What is claimed is:

1. A mutant strain of *Corynebacterium glutamicum* deposited in the China General Microbiological Culture Collection Center (CGMCC), having a deposit number of CGMCC No: 20138 wherein the mutant strain of *Corynebacterium glutamicum* is obtained by atmospheric and room temperature plasma (ARTP) mutagenesis and screening from *Corynebacterium glutamicum* with a deposit number of CGMCC1.15647 as an initial strain, wherein the mutant strain has been modified to express a N-terminal pro-peptide of human procollagen type I.

* * * * *

SEQUENCE LISTING

```
<160> NUMBER OF SEQ ID NOS: 11

<210> SEQ ID NO 1
<211> LENGTH: 720
<212> TYPE: DNA
<213> ORGANISM: Artificial Sequence
<220> FEATURE:
<223> OTHER INFORMATION: synthesized in the lab

<400> SEQUENCE: 1
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
```

```
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720
```

<210> SEQ ID NO 2
<211> LENGTH: 426
<212> TYPE: DNA
<213> ORGANISM: Artificial Sequence
<220> FEATURE:
<223> OTHER INFORMATION: synthesized in the lab

<400> SEQUENCE: 2

```
caggtccaac tgcaagaaag cggtggtggt tccgtccaag caggcggctc cctgcgtctg     60
tcctgcaccg catccggctt caccttcgac gattccgaca tgggctggta ccaccaggct    120
ccaggcaacg agtgcgagct ggtctccacc atcggcaacg acggctccac ctactacgca    180
gactccgtga agggccgctt caccatctcc cgcgacaacg caaagaacac cgtgtacctc    240
cagatgaaca acctgaagcc agaggacacc gcaatgtact actgcgcagc agatctgcac    300
ccaaccttcc gcaagtggga ttcccgcacc tccgactgct actccggccc actggagtac    360
ggctacaact actggggcca gggtacccag gtgaccgtct cttcacacca ccaccaccac    420
cactga                                                              426
```

<210> SEQ ID NO 3
<211> LENGTH: 480
<212> TYPE: DNA
<213> ORGANISM: Artificial Sequence
<220> FEATURE:
<223> OTHER INFORMATION: synthesized in the lab

<400> SEQUENCE: 3

```
caagaagaag gccaagtgga aggtcaagat gaggacatcc caccaatcac ttgcgtgcag     60
aacggtctgc gctaccacga ccgtgatgtc tggaaaccag aaccttgccg catctgcgtg    120
tgcgacaacg gcaaggtgct gtgcgacgac gtgatctgcg atgaaaccaa gaactgcccg    180
ggcgcagaag tgccagaagg cgaatgctgc ccagtgtgcc cagatggctc cgagtcccca    240
accgatcaag aaaccaccgg cgtcgagggc cctaagggcg atactggtcc tcgtggtcca    300
cgcggtccag ccggccctcc gggccgtgac ggcatcccgg ccagccggg cctcccgggc    360 ccaccgggcc caccgggccc accgggccca ccgggtctgg gcggtaactt cgcaccagat    420
tacaaggacg acgatgataa gggccaccat catcaccacc atcaccacgg cggccagtaa    480
```

<210> SEQ ID NO 4
<211> LENGTH: 26
<212> TYPE: DNA
<213> ORGANISM: Artificial Sequence
<220> FEATURE:
<223> OTHER INFORMATION: synthesized in the lab

<400> SEQUENCE: 4

```
gatatcaacg taaatgccgc ttcgcc                                         26
```

<210> SEQ ID NO 5
<211> LENGTH: 27
<212> TYPE: DNA
<213> ORGANISM: Artificial Sequence
<220> FEATURE:
<223> OTHER INFORMATION: synthesized in the lab

```
<400> SEQUENCE: 5
ctcgagaatt aattctgttt cctgtgt                                                27

<210> SEQ ID NO 6
<211> LENGTH: 21
<212> TYPE: DNA
<213> ORGANISM: Artificial Sequence
<220> FEATURE:
<223> OTHER INFORMATION: synthesized in the lab

<400> SEQUENCE: 6
aagcttatgg tgagcaaggg c                                                      21

<210> SEQ ID NO 7
<211> LENGTH: 23
<212> TYPE: DNA
<213> ORGANISM: Artificial Sequence
<220> FEATURE:
<223> OTHER INFORMATION: synthesized in the lab

<400> SEQUENCE: 7
ggatccttac ttgtacagct cgt                                                    23

<210> SEQ ID NO 8
<211> LENGTH: 29
<212> TYPE: DNA
<213> ORGANISM: Artificial Sequence
<220> FEATURE:
<223> OTHER INFORMATION: synthesized in the lab

<400> SEQUENCE: 8
aagcttatgc aggtccaact gcaagaaag                                              29

<210> SEQ ID NO 9
<211> LENGTH: 43
<212> TYPE: DNA
<213> ORGANISM: Artificial Sequence
<220> FEATURE:
<223> OTHER INFORMATION: synthesized in the lab

<400> SEQUENCE: 9
gaattctcag tggtggtggt ggtggtgtga agagacggtc acc                              43

<210> SEQ ID NO 10
<211> LENGTH: 29
<212> TYPE: DNA
<213> ORGANISM: Artificial Sequence
<220> FEATURE:
<223> OTHER INFORMATION: synthesized in the lab

<400> SEQUENCE: 10
aagcttatgc aagaagaagg ccaagtgga                                              29

<210> SEQ ID NO 11
<211> LENGTH: 30
<212> TYPE: DNA
<213> ORGANISM: Artificial Sequence
<220> FEATURE:
<223> OTHER INFORMATION: synthesized in the lab

<400> SEQUENCE: 11
gaattcttac tggccgccgt ggtgatggtg                                             30
```